(12) United States Patent
Voss

(10) Patent No.: US 7,160,309 B2
(45) Date of Patent: Jan. 9, 2007

(54) SYSTEMS FOR ANCHORING A MEDICAL DEVICE IN A BODY LUMEN

(76) Inventor: Laveille Kao Voss, 2832 Hallmark Dr., Belmont, CA (US) 94002

( * ) Notice: Subject to any disclaimer, the term of this patent is extended or adjusted under 35 U.S.C. 154(b) by 610 days.

(21) Appl. No.: 10/335,147

(22) Filed: Dec. 31, 2002

(65) Prior Publication Data
US 2004/0127913 A1    Jul. 1, 2004

(51) Int. Cl.
A61B 17/00 (2006.01)
A61B 17/04 (2006.01)
(52) U.S. Cl. .................... 606/144; 606/148; 606/1; 606/108
(58) Field of Classification Search ................ 606/213, 606/144, 148, 1, 108; 604/167.01
See application file for complete search history.

(56) References Cited

U.S. PATENT DOCUMENTS

| 5,700,273 | A |  | 12/1997 | Buelna et al. |  |
|---|---|---|---|---|---|
| 5,782,860 | A |  | 7/1998 | Epstein et al. |  |
| 5,836,955 | A |  | 11/1998 | Buelna et al. |  |
| 5,836,956 | A |  | 11/1998 | Buelna et al. |  |
| 5,846,253 | A |  | 12/1998 | Buelna et al. |  |
| 6,117,144 | A | * | 9/2000 | Nobles et al. | 606/144 |
| 6,348,059 | B1 |  | 2/2002 | Hathaway et al. |  |
| 6,632,237 | B1 | * | 10/2003 | Ben-David et al. | 606/213 |
| 6,911,034 | B1 | * | 6/2005 | Nobles et al. | 606/144 |
| 6,939,357 | B1 | * | 9/2005 | Navarro et al. | 606/145 |

* cited by examiner

Primary Examiner—Anhtuan T. Nguyen
Assistant Examiner—Elizabeth Houston

(57) ABSTRACT

A system for securing a device in tissue, having a sheath having a plurality of side openings; a rotatable element disposed within the sheath; and a plurality of curved projections extending from the rotatable element, wherein rotation of the rotatable element within the sheath pushes distal ends of each of the curved projections outwardly through one of the plurality of openings and into the tissue.

12 Claims, 11 Drawing Sheets

SYSTEMS FOR ANCHORING A MEDICAL DEVICE IN A BODY LUMEN

TECHNICAL FIELD

The present invention relates in general to systems for anchoring medical devices in body lumens, or body cavities. In particular, the present invention relates to systems for anchoring catheters in body lumens, which may include blood vessels.

BACKGROUND OF THE INVENTION

Various medical procedures require the anchoring of a medical device within a body lumen. All of these systems need to be designed so that the device can be removed at the end of the procedure without causing unacceptable amounts tissue damage. For example, in the case of a catheter anchored in a blood vessel, the catheter must be easily inserted through an opening in the side of the vessel yet also be easily anchored when positioned at its desired location in the vessel.

A variety of systems have been designed to anchor a catheter passing into a body lumen through an opening in the side of the body lumen. Most commonly, an inflatable balloon is mounted on the catheter. After the catheter has been positioned at a desired location, the balloon is inflated. The balloon thereby pushes against the walls of the body lumen adjacent to the side opening when the catheter is pulled back, thus holding the catheter in position. Unfortunately, a problem with using such an inflatable balloon is that it typically blocks fluid flow through the lumen, which may not be desirable. Also, in addition to inhibiting fluid circulation, the balloon may interfere with drug delivery systems in the catheter.

What is instead desired is a simple system for securing a medical device such as a catheter in a body lumen. Such a system would preferably not interfere with fluid flow through the body lumen (such as blocking fluid flow with an inflatable balloon). In addition, such an anchoring system would preferably be easily removable at the end of the medical procedure.

SUMMARY OF THE INVENTION

The present invention provides a versatile system for securing a medical device (such as a catheter) at preferred locations within a body lumen (such as a blood vessel) without blocking or substantially inhibiting fluid flow through the lumen.

In preferred embodiments, the present invention includes a sheath having a plurality of side openings; a rotatable element disposed within the sheath; and a plurality of curved projections extending from the rotatable element, wherein rotation of the rotatable element with respect to the sheath pushes distal ends of each of the curved projections outwardly through one of the plurality of openings. In preferred methods of use, the plurality of curved projections are extended outwardly from the rotatable element and are then used to brace against the tissue surrounding a side hole opening into the vessel. Thus, when the device is deployed within the body lumen, and then pulled back (ie: proximally), the curved projections contact the tissue surrounding the side opening into the vessel, thereby preventing the device from being removed. The deployed projections may also provide needle receiving locations in the case of a suturing device, such as a device for suturing an arteriotomy.

The present invention also includes an embodiment including a sheath having only one side opening with one curved projection extending from the rotatable element. Similar to the above design, rotation of the rotatable element with respect to the sheath pushes the distal end of the curved projection outwardly through the side opening. In this embodiment, the curved projection may be a wire having one end attached to the rotatable element.

In optional preferred embodiments, the curved projection(s) may be biased to spring radially outwardly as they pass through the side opening(s) in the sheath. Alternatively, or in addition, the curved projection(s) may be formed from a shape memory material which assists them in springing radially outwards as they pass through the side opening(s) in the sheath.

In various embodiments, the curved projection(s) may either be attached to the rotatable element, or they may be integrally formed into the rotatable element.

In various preferred embodiments, the curved projections are opposite ends of a deformable element such as a wire or ribbon. Most preferably, such deformable element passes through (or is fitted around) the central rotatable element.

The present invention also provides a method of anchoring a device in a body lumen or cavity, including inserting the device into the body lumen or cavity, and rotating the rotatable element with respect to the sheath, thereby causing the distal ends of each of the curved projections to move outwardly through one of the one or more openings and into the body lumen or cavity. In preferred embodiments of the present method, the body lumen may be any blood vessel.

DETAILED DESCRIPTION

FIGS. 1A to 3B illustrate a first embodiment of the invention which deploys two curved projections that can be used as an anchor against tissue surrounding an opening into a vessel lumen. In this particular example, the two curved projections are opposite ends of a single ribbon shaped element which passes through a central rotatable element of the device. The present invention is not so limited. Rather, other embodiments are also contemplated.

Figure 5A:
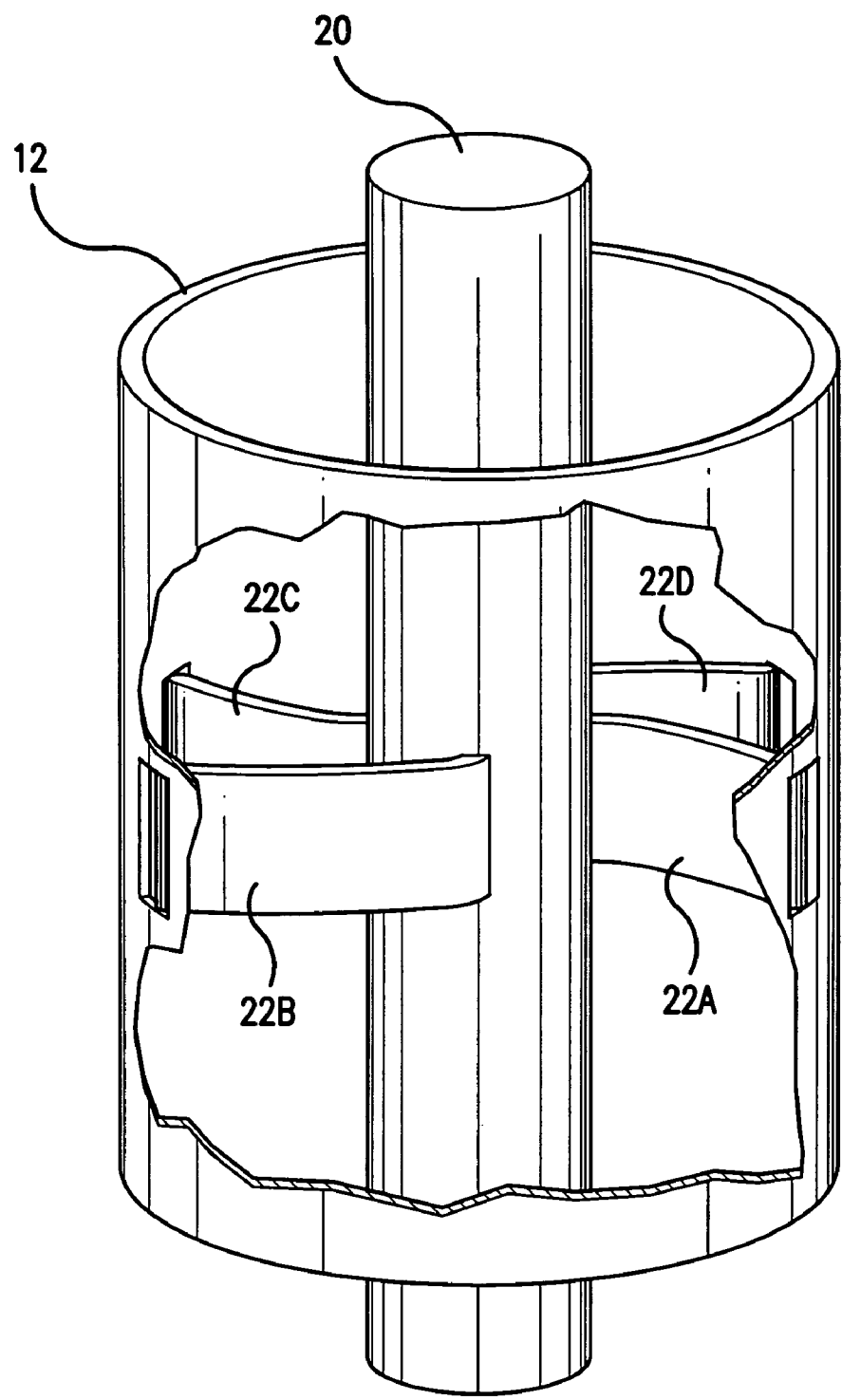
FIG. 5A is a perspective view of a third embodiment of the invention prior to its deployment.
Figure 5B:
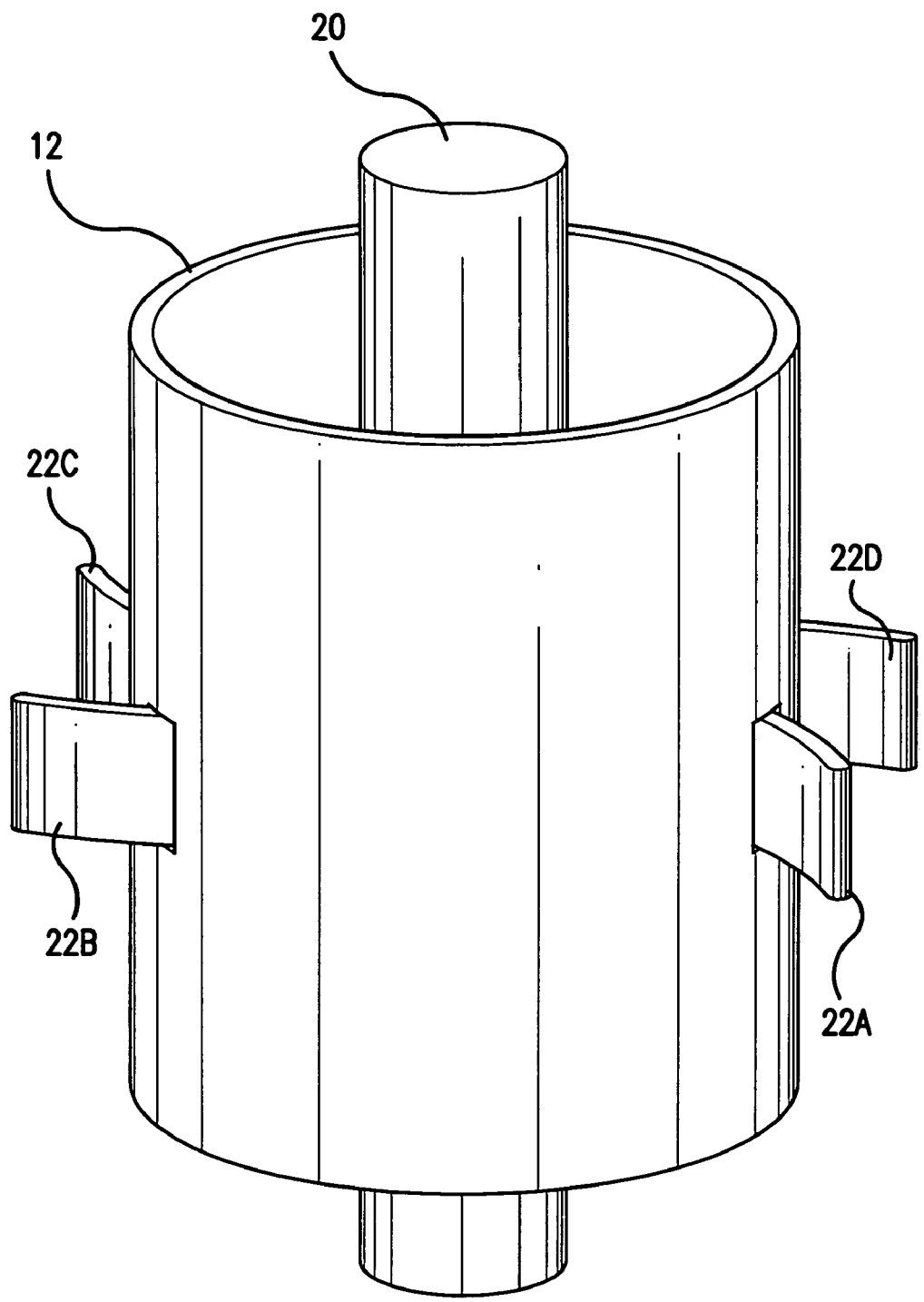
FIG. 5B is a perspective view of the third embodiment of the invention after it has been deployed.
Figure 6A:
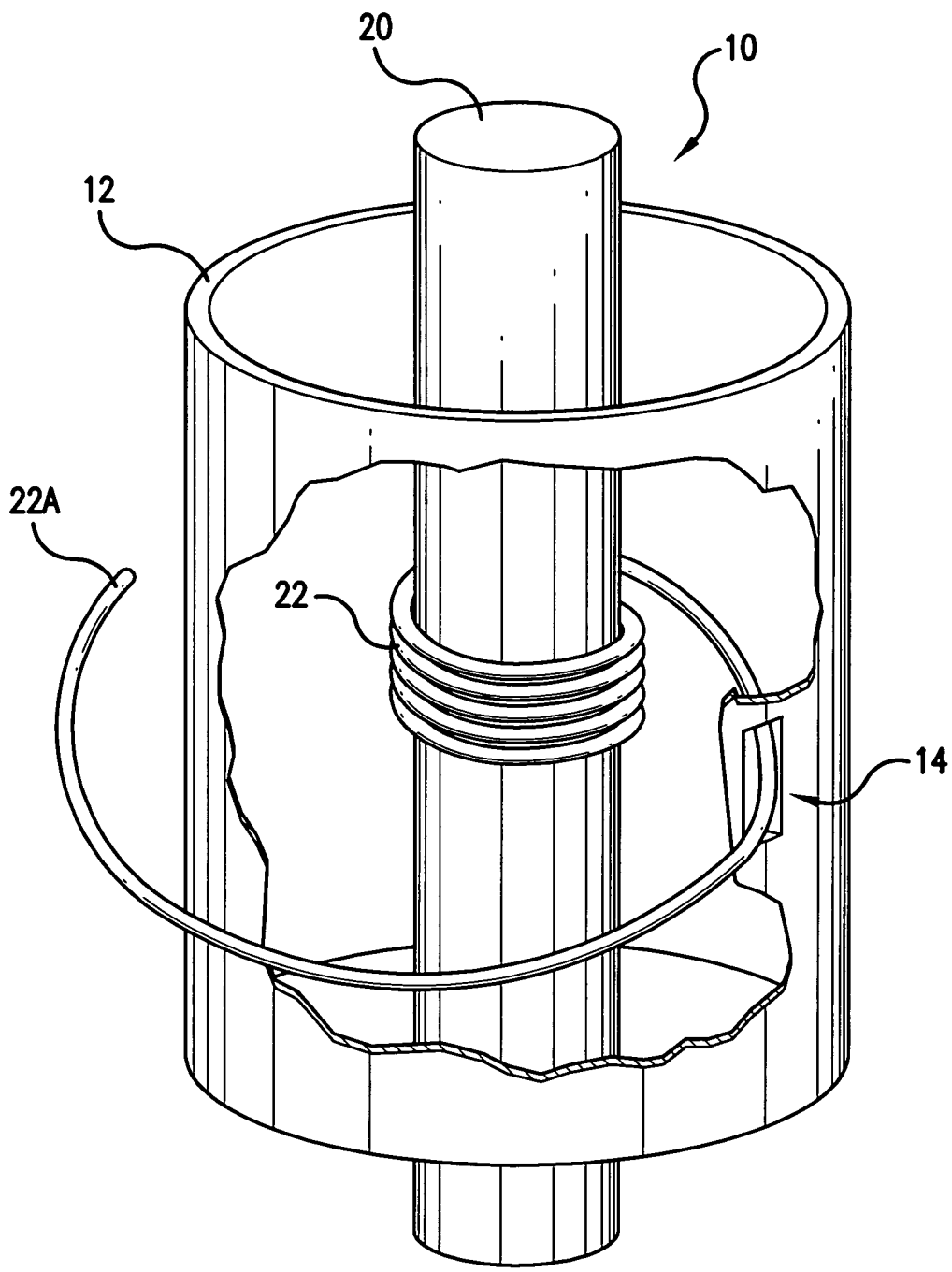
FIG. 6A is a perspective view of a fourth embodiment of the invention having only one side opening in the sheath.
Figure 6B:
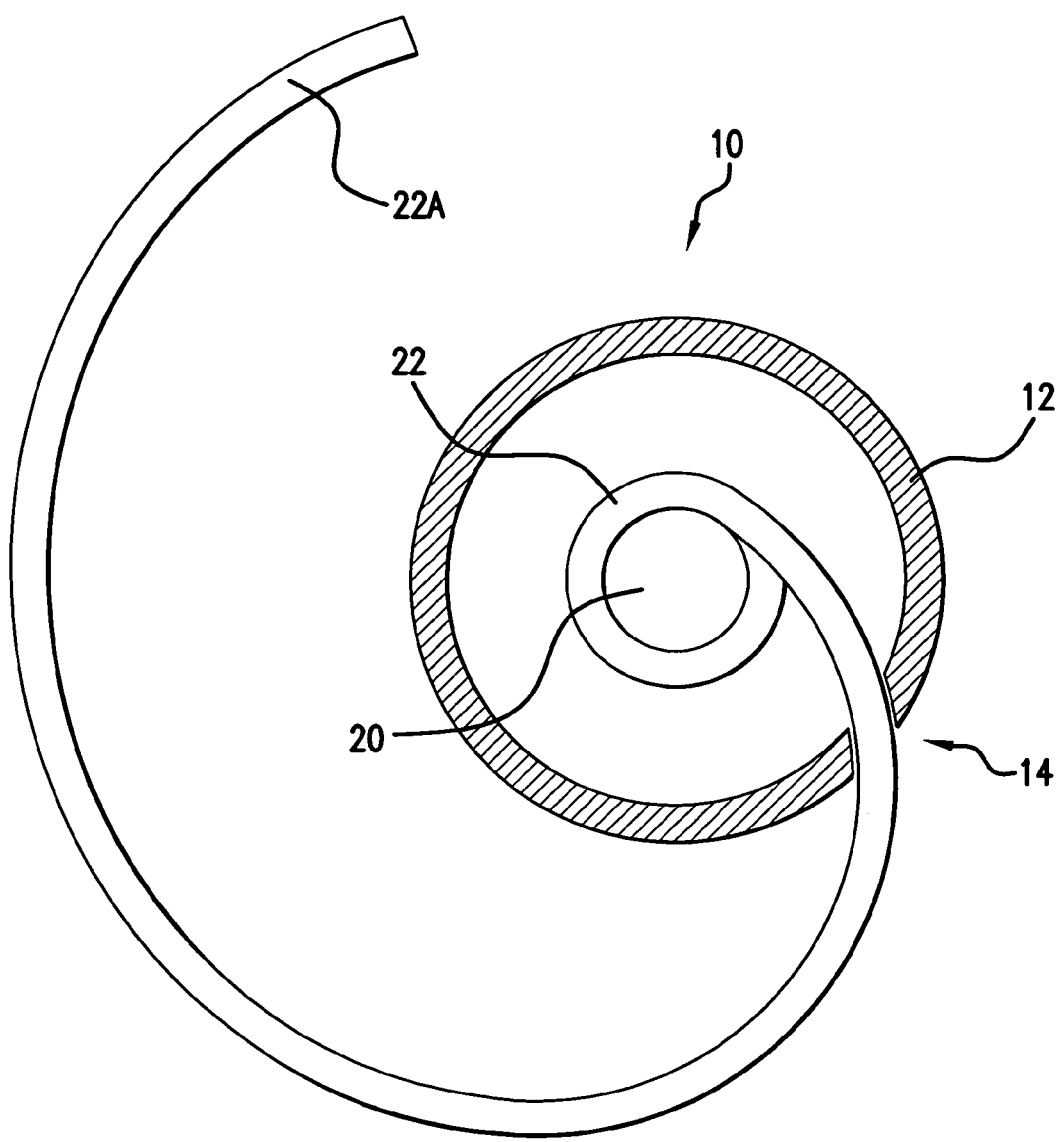
FIG. 6B is a sectional elevation view corresponding to FIG. 6A.
Figure 7A:
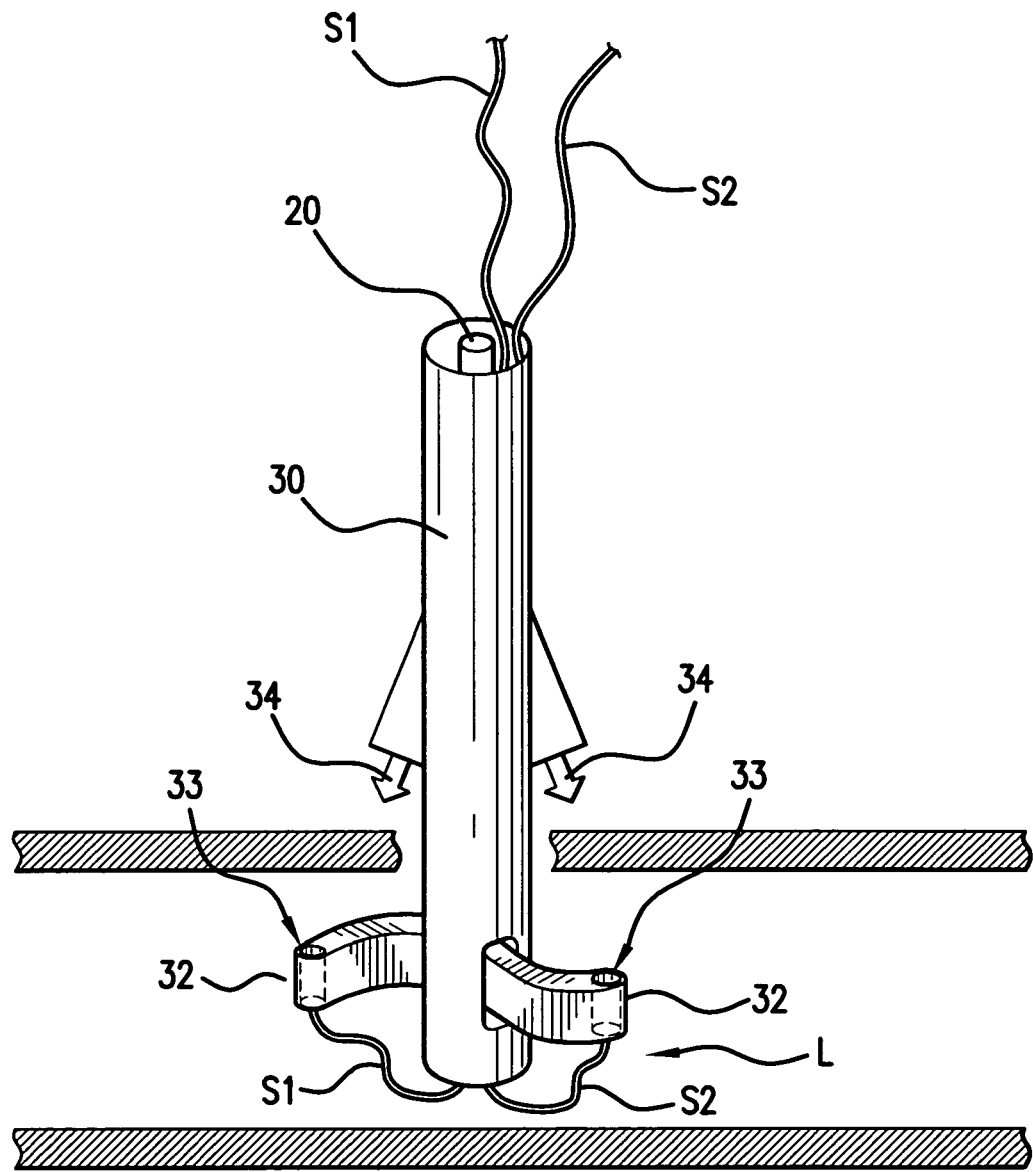
FIG. 7A is a perspective view of a fifth embodiment of the invention, in which the invention comprises a suturing device, after its arms have been deployed, but prior to suturing a tissue hole.
Figure 7B:
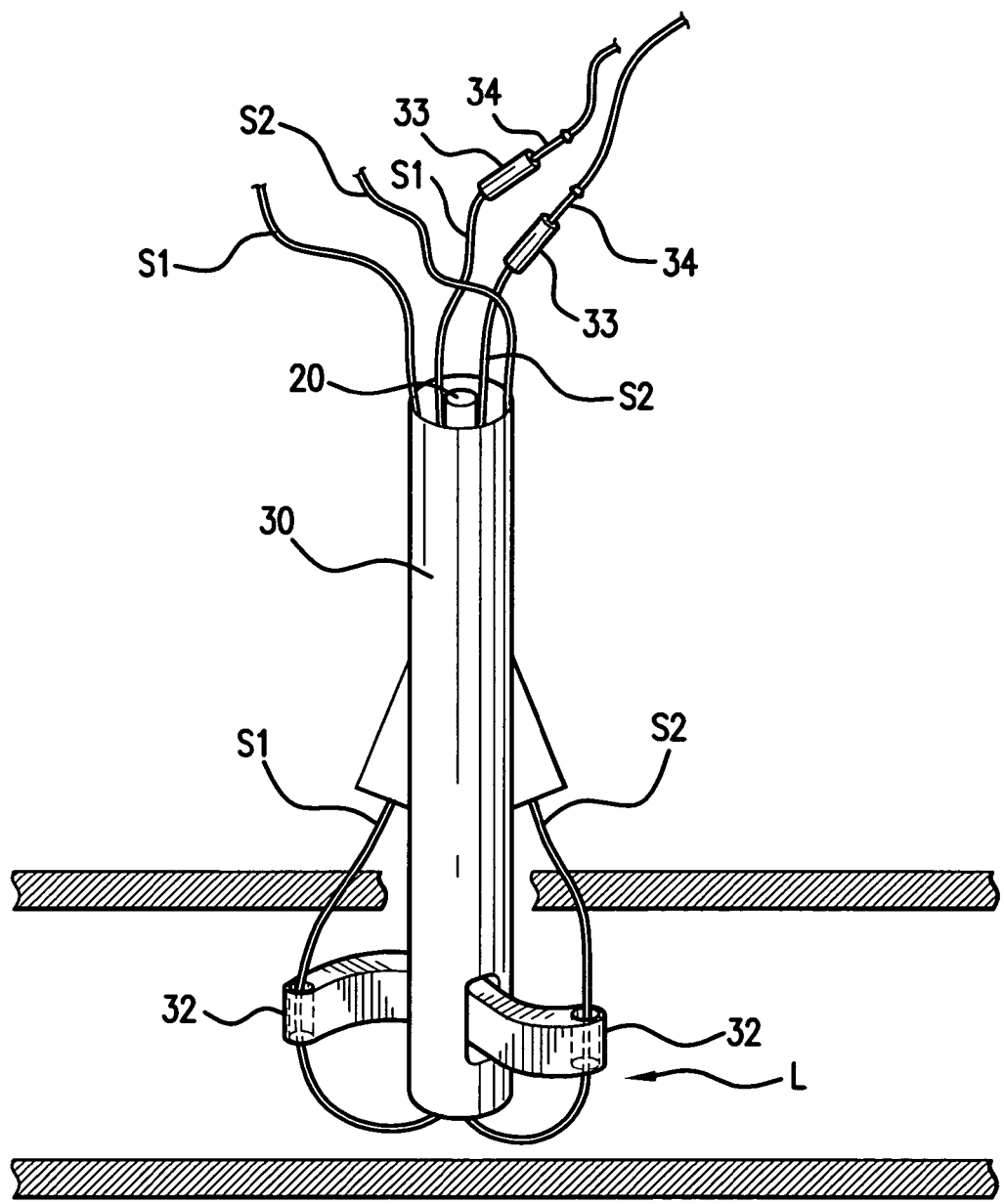
FIG. 7B is a perspective view corresponding to FIG. 7A, but after the tissue hole has been sutured.

For example, FIGS. 4A and 4B illustrate a second embodiment of the invention which deploys four curved projections. This embodiment is similar to the first embodiment, but instead uses two ribbon shaped elements which are spaced longitudinally apart from one another. FIGS. 5A and 5B illustrate a third embodiment of the invention which deploys four curved projections into the tissue. In this particular example, the curved projections may either be attached to the central rotatable element, or may be integrally formed with the central rotatable element. FIGS. 6A and 6B illustrate a fourth embodiment of the invention which deploys a single curved projection in the form of a wire attached at one end to the central rotatable element. Lastly, FIGS. 7A and 7B illustrate a fifth embodiment of the invention in which a suturing device includes needles and suture in operative relationships with the anchoring elements or projections.

Each of the four embodiments of the invention (FIGS. 1A to 6B) illustrate the present invention as incorporated into a catheter system. Thus, for clarity, each of FIGS. 1A, 1B, and 4 to 6B illustrates only a cut-out longitudinal section of a catheter system in which the present invention is incorporated. FIGS. 3A and 3B show a greater length of the catheter. As can be appreciated, the catheter extends upwardly and/or downwardly perpendicular from the page in FIGS. 2A and 2B.

Figure 1A:
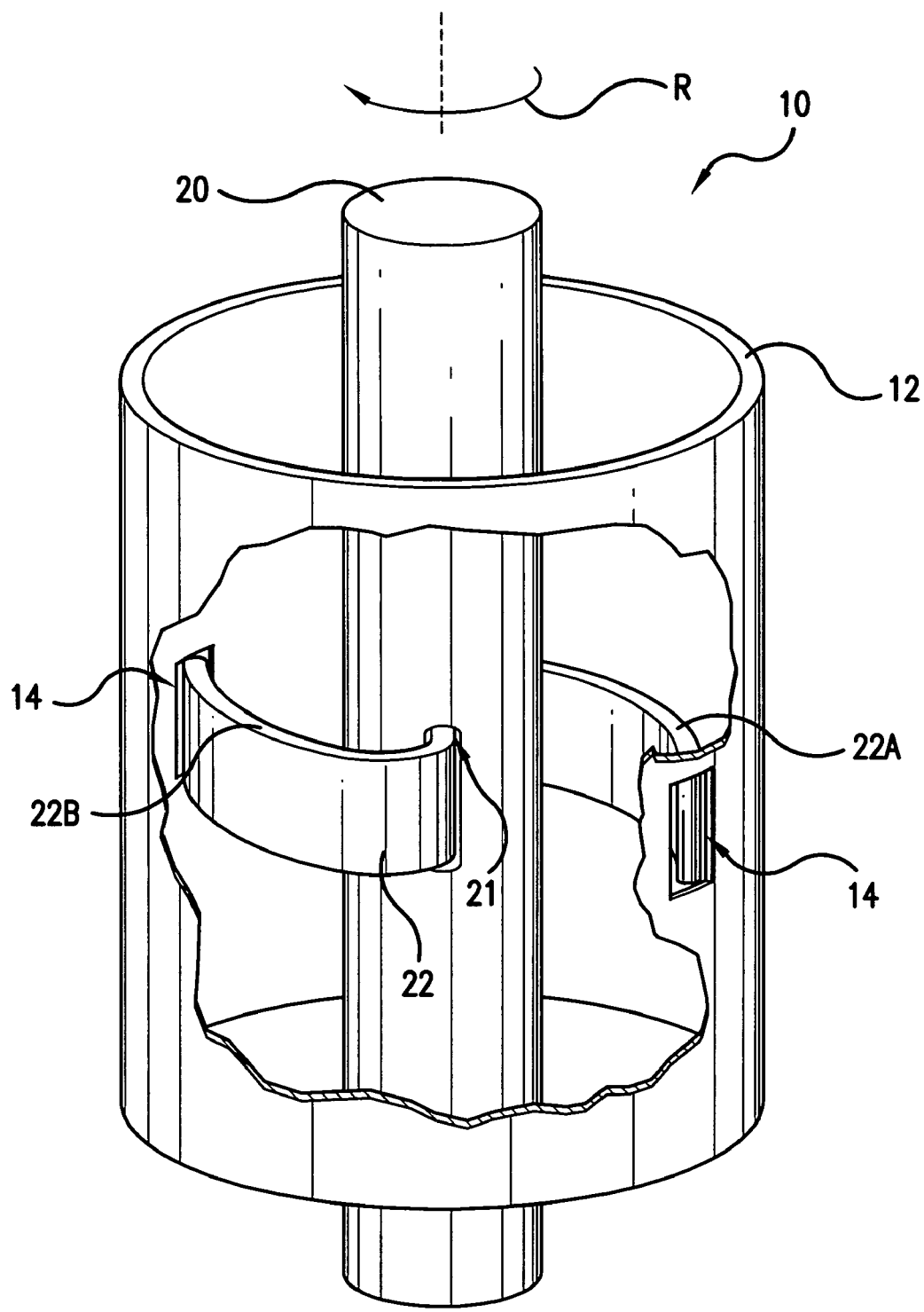
FIG. 1A is a perspective view of a first embodiment of the invention prior to its deployment.
Figure 2A:
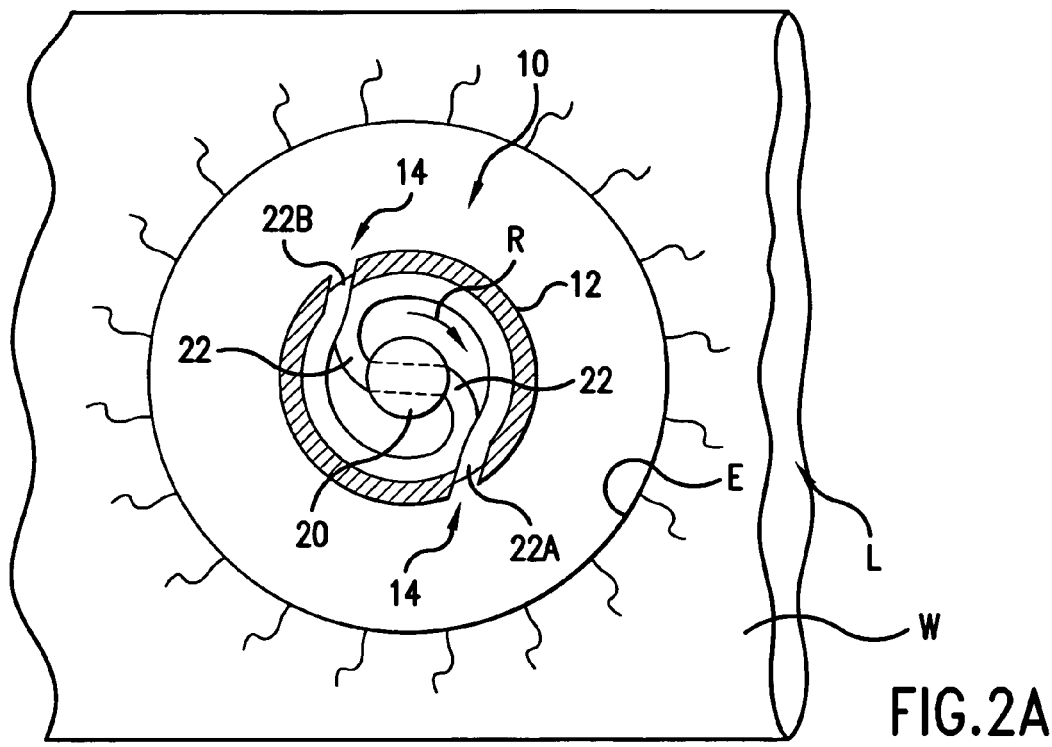
FIG. 2A is a top plan view corresponding to FIG. 1A, showing the device passing through a side opening in a vessel lumen, with the distal end of the device positioned within the vessel lumen.
Figure 3A:
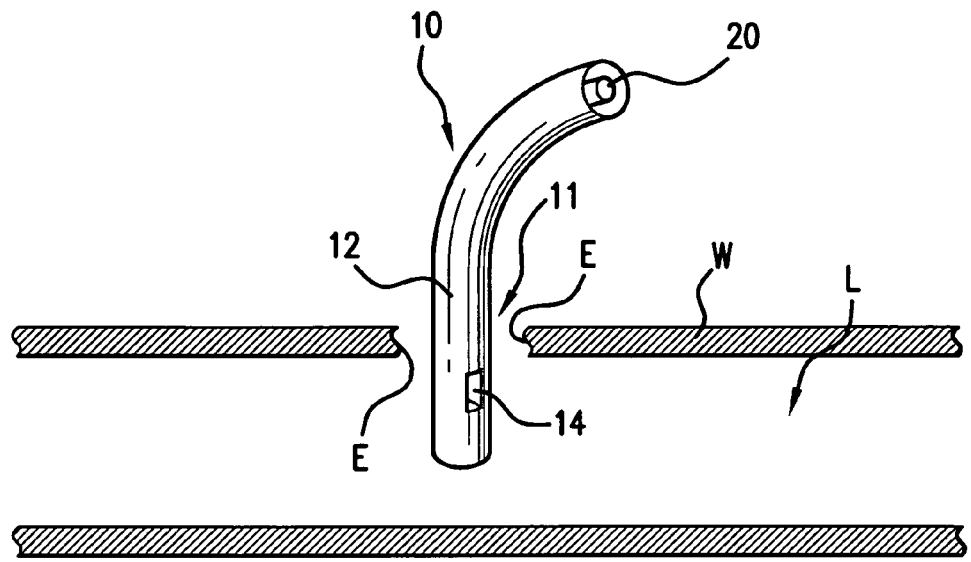
FIG. 3A is a side view corresponding to FIG. 2A.
Figure 3B:
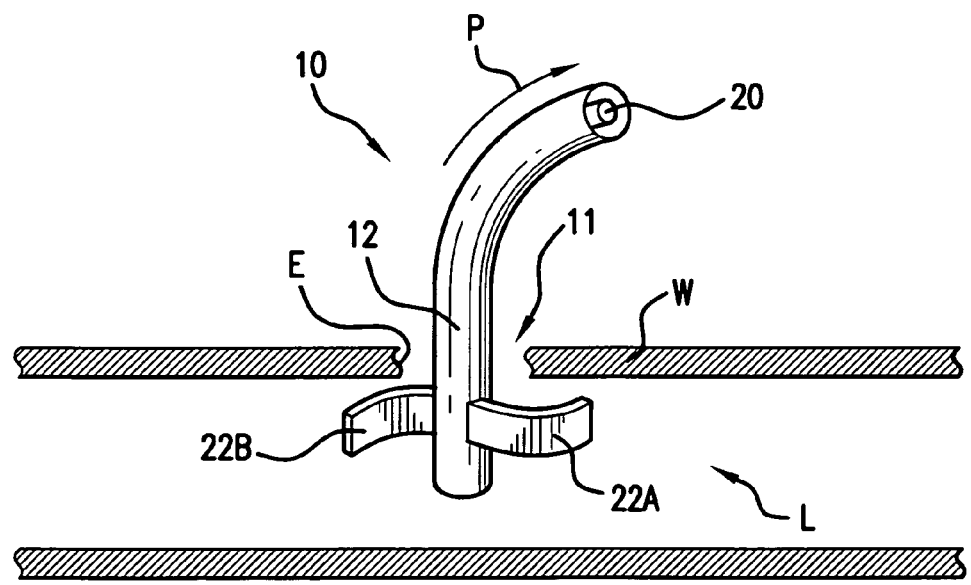
FIG. 3B is a side view corresponding to FIG. 2B.

Referring first to FIGS. 1A, 2A and 3A, a system 10 for securing a catheter system in a body lumen is provided. Sheath 12 has a pair of side openings 14 disposed on opposite sides thereof. A central rotatable element 20 is received within sheath 12. A pair of projections 22A and 22B extend radially outwardly from rotatable element 20, as shown in FIGS. 1A, 2A and 3A. The sheath described herein may be a portion of a catheter body, an introducer sheath, or simply a hollow tubular body that is part of a device into which the present invention is incorporated. As will also be explained and illustrated, the present invention may be used in applications other than in a catheter body. For example, the present invention may be incorporated into a suturing device as shown in FIGS. 7A and 7B. It is to be understood, however, that the present invention may be incorporated into other devices as well.

Figure 1B:
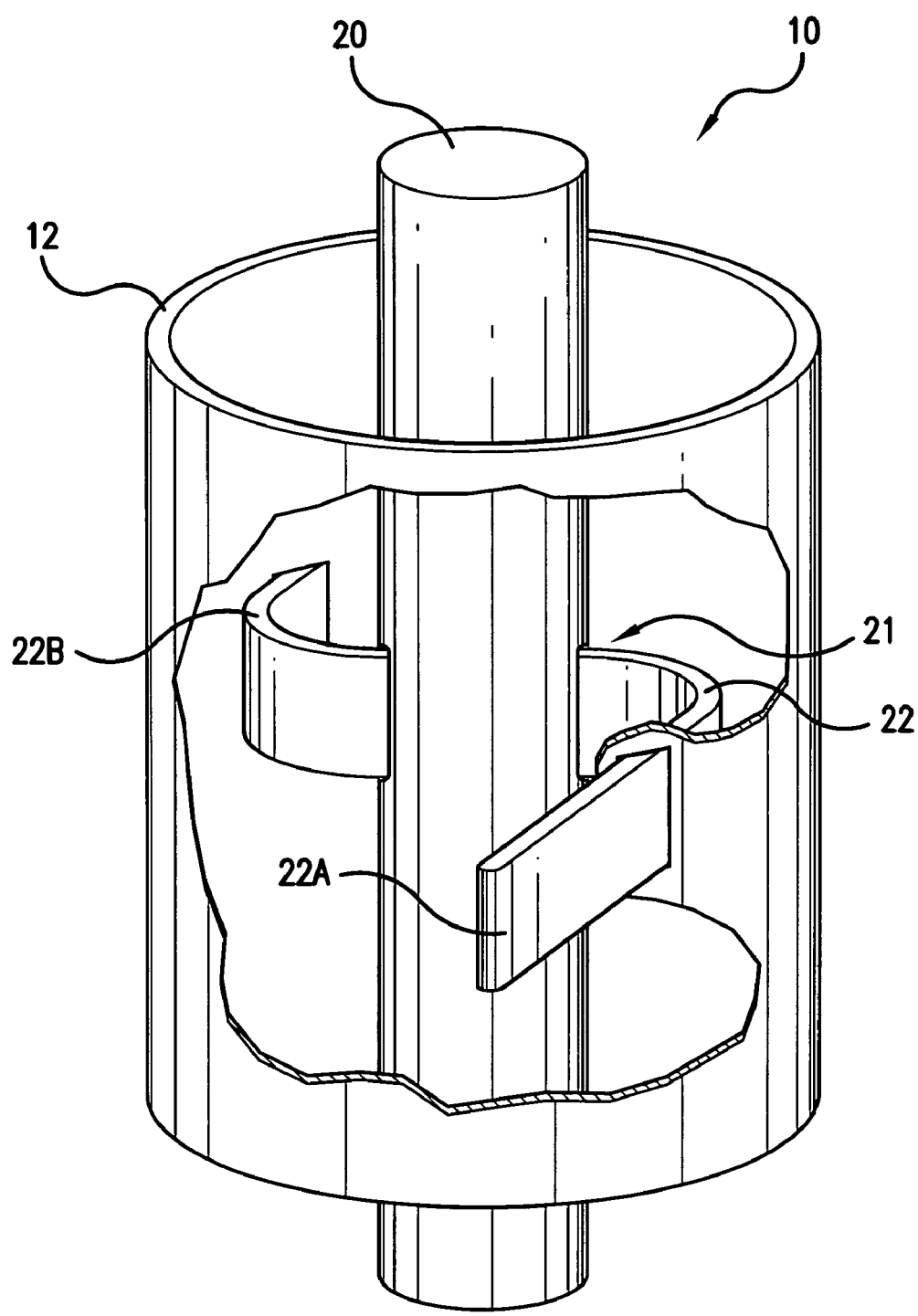
FIG. 1B is a perspective view of the first embodiment of the invention after it has been deployed.
Figure 2B:
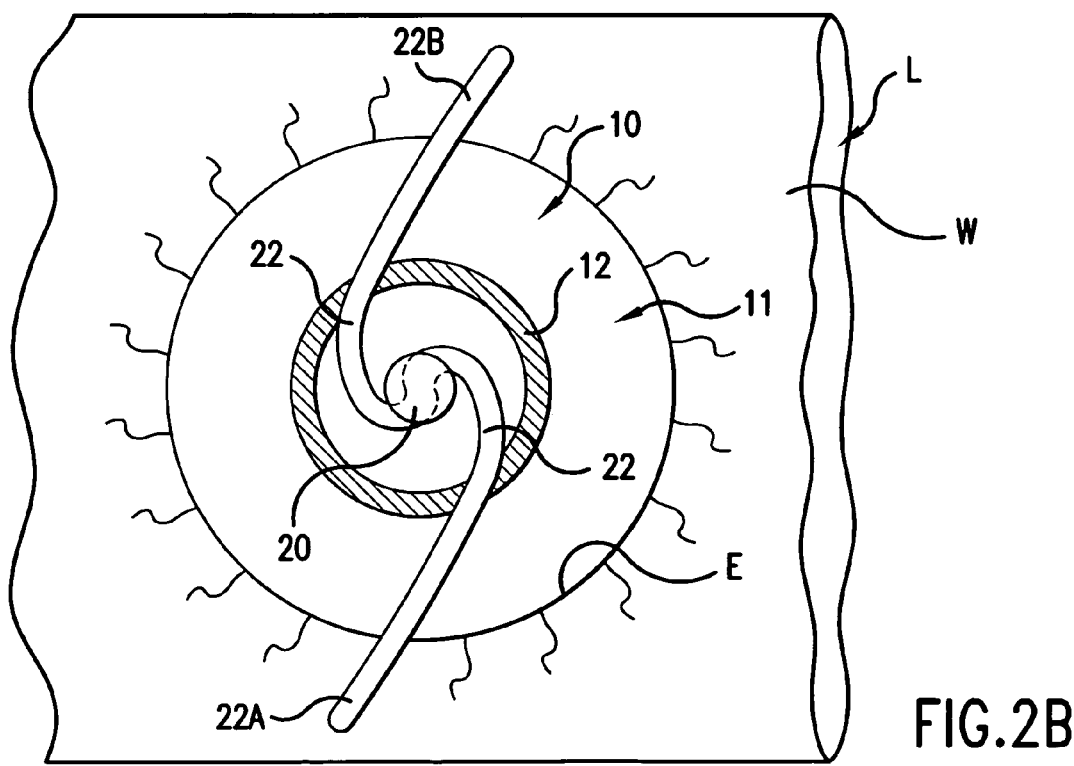
FIG. 2B is a top plan view corresponding to FIG. 1B, showing the device passing through a side opening in a vessel lumen, with the distal end of the device anchored in the vessel lumen.

Returning to FIGS. 1A, 2A and 3A, rotation of rotatable element 20 within sheath 12 in direction R (FIG. 2A) causes the distal ends of each of projections 22A and 22B to be pushed out through openings 14. Thus, rotation of rotatable element 20 with respect to sheath 12 in direction R moves curved projections 22A and 22B from the pre-deployed position (FIGS. 1A, 2A and 3A) to the fully deployed position (FIGS. 1B, 2B and 3B). As can be seen in FIG. 3B, such deployment causes curved projections 22A and 22B to extend beyond the edges E of side hole 11 in the wall W of body lumen L. Thus, curved projections 22A and 22B can act as an anchoring system, such that they will push against the interior surface of wall W when the catheter system 10 is pulled proximally in direction P.

It is to be understood that all reference herein made to rotation of the rotatable element (which is disposed within the sheath) both in the specification and claims, refers to rotation of the rotatable element with respect to the sheath. Thus, "rotation of the rotatable element" in the specification and claims, encompasses rotation of the rotatable element with the sheath held stationary, rotation of the sheath with the rotatable element held stationary, rotation of the sheath and rotatable element in opposite directions, and rotation of the sheath and rotatable element in the same direction, but at different speeds.

As can be appreciated, removal of the present anchoring system is accomplished by simply rotating rotatable element 20 with respect to sheath 12 in a direction opposite to R, thereby retracting curved projections 22A and 22B into the sheath.

As shown in FIGS. 1A to 3B, curved projections 22A and 22B move through side openings 14 which are disposed on opposite sides of sheath 12. Thus, in various embodiments, any number of side openings 14 may be disposed equidistantly around the circumference of sheath 12.

Projections 22A and 22B may be curved. The projections preferably extend radially from the rotatable element in a plane that may be perpendicular or otherwise transverse to the longitudinal axis of the device or to the rotatable element. Specifically, the projections 22A and 22B move through side openings 14 as the projections are deployed in a radial direction with respect to the axis of the device. Such movement in the radial direction may preferably be confined to movement in the transverse plane defined by the lengths of the projections.

In the preferred embodiment illustrated in FIGS. 1A to 3B, projections 22A and 22B are simply opposite ends of a single deformable member 22 which passes through a hole 21 in rotatable element 20. Deformable member 22 (and its curved projections 22A and 22B) may be formed from a ribbon shaped material (having a rectangular cross section, as shown). Alternatively, deformable member 22 (and its curved projections 22A and 22B) may be formed from a wire (having a circular cross section). In further embodiments, deformable member 22 (and its curved projections 22A and 22B) may be formed from a member having an I-beam cross section.

An advantage of curved projections 22A and 22B being ribbon shaped or I-beam shaped (or any other dimension in which they are thicker in the direction along the length of sheath 12) is that they are more resistant to bending when the catheter is pulled in direction P, such that the projections push against the tissue surrounding the interior of opening 11 through tissue wall W (see FIG. 3B).

It is to be understood that although curved projections 22A and 22B may be opposite ends of a single deformable member 22 (as shown), curved projections 22A and 22B may also be two separate elements which either are fastened to rotatable element 20 or are integrally formed from the same block of material as rotatable element 20. Whether or not curved projections 22A and 22B are opposite ends of a single member, or are separate elements, such curved projections are preferably formed from a deformable material. Suitable deformable materials may include (but are not limited to) metals, including shape memory metals, polymers, or any combinations thereof.

In optional preferred embodiments, curved projections 22A and 22B may be formed of a material which causes them to be biased such that their ends spring radially outwardly (i.e.: straighten out) as they pass through side openings 14. An example of this effect can be seen in FIG.

2B where the curved radially extending ends of projections 22A and 22B are shown as being straighter than the center portion of deformable member 22 that is inside sheath 12. This is advantageous in that it is the straightest portion of deformable member 22 protrudes radially away from the center of the device, and reaching farther, thus maximizing the amount of tissue against which the projections are anchored.

Optionally, curved projections 22A and 22B may be formed of a shape memory material (such as Nitinol). As such, curved projections 22A and 22B may thus be formed to spring radially outwardly (i.e.: straighten out) when they are exposed to a temperature change. For example, curved projections 22A and 22B could be exposed to a temperature change as they exit windows 14 by being warmed by the fluid passing through the body lumen.

Figure 4:
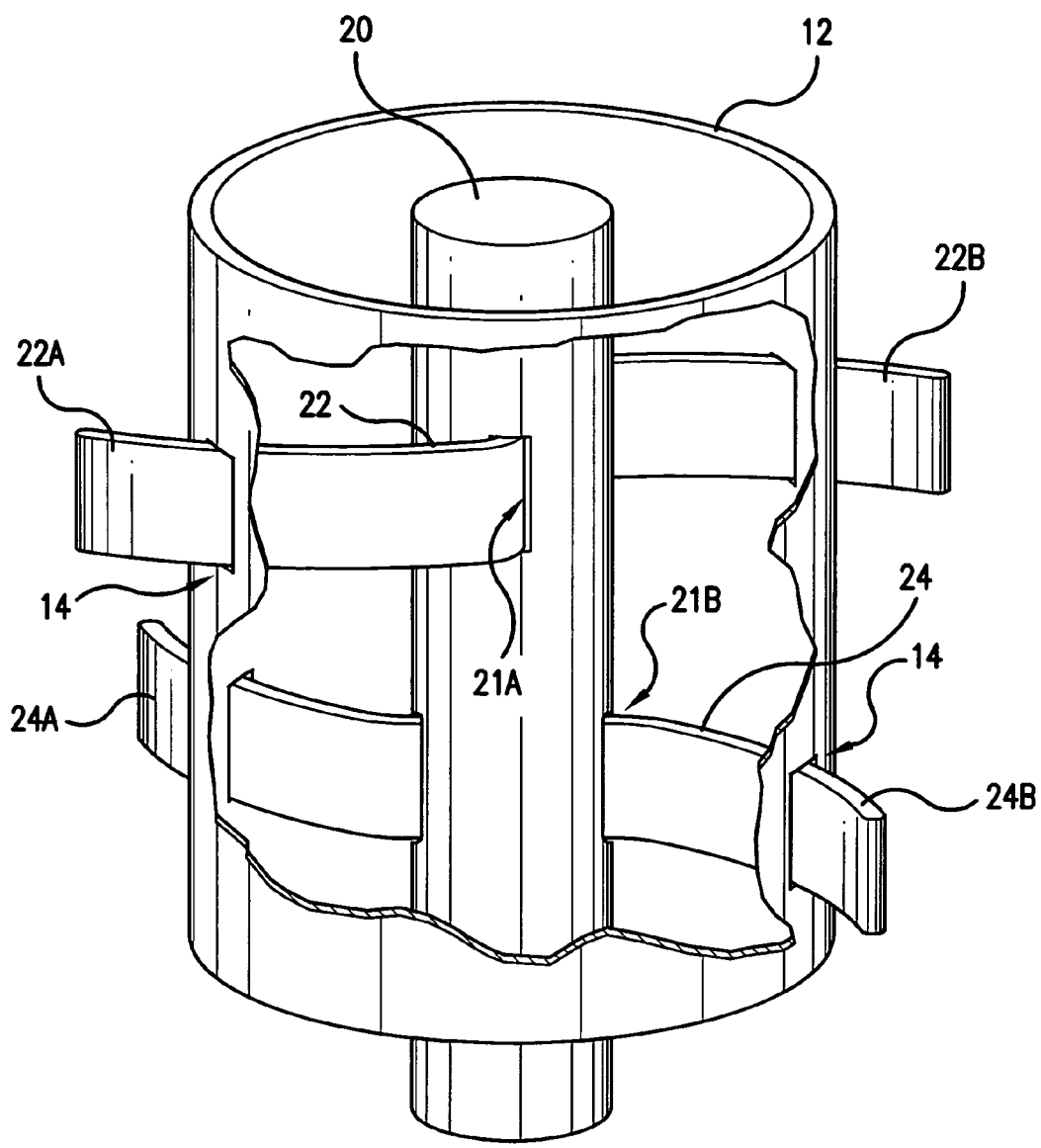
FIG. 4 is a perspective view of a second embodiment of the invention.

FIG. 4 illustrates an embodiment of the invention having two pairs of curved projections. Specifically, a first pair comprising curved projections 22A and 22B, and a second pair comprising curved projections 24A and 24B. Thus, in this embodiment side openings 14 are also disposed longitudinally along the length of the sheath (as well as about the circumference of the shaft). As illustrated, curved projections 22A and 22B are opposite ends of a first deformable element 22 passing through hole 21A while 24A and 24B are opposite ends of a second deformable element 24 passing through hole 21B.

FIGS. 5A and 5B illustrate yet another embodiment of the invention in which four curved projections 22A, 22B, 22C and 22D each extend from central rotatable element 20. In this embodiment, four curved projections are used. It is to be understood however that, in accordance with the present invention, any plurality of curved projections can be used. These curved projections protrude through openings which may be disposed equidistantly around the circumference of shaft 12. For example, curved projections 22A, 22B, 22C and 22D are shown as disposed at 90 degrees to one another.

FIGS. 6A and 6B illustrate yet another embodiment of the invention in which a single curved projection 22A is deployed through a single side opening 14. In this embodiment, curved projection 22A is one end of a wire (or other suitable deformable member) 22 which is wrapped around (and attached at one end to) central rotatable element 20. In this embodiment, the length of wire 22 may optionally be as long, or longer than, deformable member 22 as shown in the other embodiments. Thus, wire 22 can be rotated such that its distal end (curved projection 22A) is deployed much father through side opening 14 than is shown in the previous embodiments. This would have the effect of causing wire 22, and its distal end (i.e. curved projection 22A) to extend farther around the circumference of sheath 12, thus firmly anchoring the present device in position. FIGS. 6A and 6B show wire 22 extending approximately half way around the circumference of the device. It is to be understood that the distal end of wire 22 (i.e. curved projection 22A) may also extend even further around the circumference of the device. For example, the distal end of wire 22 may be extended fully around the device, or even further (so that it wraps around the circumference of the device several times).

In various embodiments, the present invention is substantially enclosed within the body of the catheter, thus saving space and permitting easy access into the interior of body lumen L.

In various preferred embodiments, the present system is dimensioned to be around 5 to 10 mm in diameter, but may instead be dimensioned smaller so that it may fit into vessels less than 5 mm in diameter.

The various embodiments of the invention which are incorporated into a catheter system do not block fluid flow when anchoring a catheter in a body lumen. Thus, the present invention may conveniently be used in conjunctions with systems either for drug or therapeutic energy delivery, or with diagnostic systems.

In an alternate embodiment, shown in FIGS. 7A and 7B, the service is a suturing device 30 that is anchored on the interior side of a vessel wall through an arteriotomy. The device 30 may include suture-carrying or holding features located on extendable projections 32 in order to retrieve sutures S1 and S2 when device 30 provides an arteriotomy closure. In accordance with this embodiment, projections 32 are deployed radially outwardly in the same fashion that projections 22 were deployed in the previously described embodiments (eg: by rotating rotatable element 20 within device 30).

The suture-carrying features may be recesses formed in projections 32. For example, the suture-carrying features may include cuffs 33 that may be attached to the ends SI and S2 of a length of suture which runs through the center of device 30. Cuffs 33 can be held within recesses in projections 32. The present suture-carrying features may include cuffs, but the present invention is not so limited. For example, the ends of the suture can alternatively be formed into other features that are connectable to needles, such as loops. Suturing device 30 further comprises a pair of needles 34 that are initially disposed on an exterior of lumen L as shown in FIG. 7A. Thereafter, needles 34 are advanced so that they pass through the wall of the vessel, such that each needle 34 is received into a cuff 33. Thereafter, needles 34 are retracted, as shown in FIG. 7B, each pulling a cuff 33 with a length of suture (S1 or S2) attached thereto out of the proximal end of device 30. Thereafter, extendable projections 32 can be retracted radially inwardly (by rotating element 20 in an opposite direction) so that the distal end of device 30 may be removed from the hole in the side of the artery, leaving behind suture passing therethrough, which can be used to close the hole. It is to be understood that although device 30 is illustrated as having two needles 34, cuffs 33 and sutures S1 and S2, other embodiments having more needles, cuffs and sutures are also possible. As illustrated in FIGS. 7A and 7B, the needles of such a device are would engage the cuffs and pull the suture through tissue.

What is claimed is:

1. A system for anchoring a device in a body lumen or cavity, comprising:
   a generally cylindrical sheath having a plurality of sidewall openings disposed equidistant around a circumference of the sheath, and having a proximal end, a distal end and a longitudinal axis extending therebetween;
   a rotatable element disposed within the sheath, the rotatable element rotating about the longitudinal axis of the sheath; and
   a plurality of projections extending radially from the rotatable element and moving transverse to the longitudinal axis of the sheath, at least one of the plurality of projections extending outwardly into the body lumen or cavity through at least one of the plurality of sidewall openings in a radial direction with respect to the longitudinal axis of the sheath, transverse to the axis of the sheath, as the rotatable element is rotated.

2. The system of claim 1, wherein at least one of the plurality of projections is curved, the curved projections having a geometry complementary to the generally cylindrical sheath.

3. The system of claim 1, wherein at least one of the plurality of projections is made of a deformable material.

4. The system of claim 3, wherein the at least one projection comprises curved projections on opposite ends of a deformable element.

5. The system of claim 4, wherein the deformable element passes through a hole in the rotatable element.

6. The system of claim 4, wherein at least one of the plurality of projections has a wire-shaped cross section.

7. The system of claim 4, wherein the deformable element has a ribbon shaped cross section.

8. The system of claim 4, wherein the deformable element has an I-beam shaped cross section.

9. The system of claim 1, wherein at least one of the plurality of projections is biased to spring radially outwardly as it passes outwardly through at least one of the plurality of sidewall openings as the rotatable element is rotated with respect to the sheath.

10. The system of claim 1, wherein at least one of the plurality of projections comprises a pair of projections disposed on opposite sides of the rotatable element.

11. The system of claim 1, further comprising:

a suture-carrying feature on the ends of at least one of the plurality of projections.

12. The system of claim 11, wherein the suture-carrying feature is a suture cuff.

* * * * *

UNITED STATES PATENT AND TRADEMARK OFFICE
CERTIFICATE OF CORRECTION

PATENT NO. : 7,160,309 B2  
APPLICATION NO. : 10/335147  
DATED : January 9, 2007  
INVENTOR(S) : Laveille Kao Voss Page 1 of 1

It is certified that error appears in the above-identified patent and that said Letters Patent is hereby corrected as shown below:

<u>Column 6</u>  
Line 20, change "SI" to --S1--  
Line 43, after "device", remove "are"

Signed and Sealed this

Sixth Day of November, 2007

JON W. DUDAS  
*Director of the United States Patent and Trademark Office*